United States Patent [19]
Fernandez et al.

[11] Patent Number: 6,133,435
[45] Date of Patent: Oct. 17, 2000

[54] AGL15 SEQUENCES IN TRANSGENIC PLANTS

[76] Inventors: Donna E. Fernandez, 1034 McKenna Blvd., Unit #5, Madison, Wis. 53719; Gregory R. Heck, 2200 Divot Dr., Crystal Lake Park, Mo. 63131-3201

[21] Appl. No.: 08/904,284

[22] Filed: Jul. 31, 1997

Related U.S. Application Data

[60] Provisional application No. 60/031,205, Nov. 21, 1996.

[51] Int. Cl.$^7$ .............................. C12N 5/04; C12N 15/29; C12N 15/82; A01H 4/00
[52] U.S. Cl. ..................... 536/23.6; 435/69.1; 435/468; 435/411; 435/419; 435/469; 435/410; 800/306; 800/278; 800/290; 800/295; 800/298
[58] Field of Search ................... 536/23.6; 435/252.2, 435/320.1, 418, 419, 69.1, 468, 411, 469, 410; 800/205, 250, 306, 278, 290, 295, 298

[56] References Cited

U.S. PATENT DOCUMENTS 5,177,307  1/1993  Houck et al. .

FOREIGN PATENT DOCUMENTS

| 0 409 628 | 1/1991 | European Pat. Off. . |
| WO95/01439 | 1/1995 | WIPO . |
| WO96/11566 | 4/1996 | WIPO . |
| WO96/21027 | 7/1996 | WIPO . |

OTHER PUBLICATIONS

G. C. Angenent et al., "A Novel Class of MADS Box Genes Is Involved in Ovule Development in Petunia," *Plant Cell*, 7 1569–1582 (1995).
N. Bechtold et al., "In planta Agrobacterium Medicated Gene Transfer by Infiltration of Adult *Arabidopsis thaliana* Plants,"*Comptes Rendus de l'Academie des Sciences Serie III Sciences de la Vie*, 316 1194–1199 (1993).
T. Jack et al., "Arabidopsis Homeotic Gene APETALA3 Ectopic Expression: Transcriptional and Posttranscriptional Regulation Determine Floral Organ Identity," *Cell*, 76 703–716 (1994).
P. Liang et al., "Differential Display of Eukaryotic Messenger RNA by Means of the Polymerase Chain Reaction," *Science*, 257 967–971 (1992).
S. E. Perry et al., "Envelope Membrane Proteins That Interact with Chloroplastic Precursor Proteins," *Plant Cell*, 6 93–105 (1994).
Z. Schwarz–Sommer et al., "Genetic Control of Flower Development by Homeotic Genes in *Antirrhinum majus*," *Science*, 250 931–936 (1990).
H. Sommer et al., "Deficiens, A Homeotic Gene Involved in the Control of Flower Morphogenesis in *Antirrhinum majus*: The Protein Shows Homology to Transcription Factors," *EMBO J.*, 9 605–613 (1990).
W. Y. Tang, "Blot Affinity Purification of Antibodies," Chapter 5 in *Methods in Cell Biology*, 37 95–104 (1993).
Matzke and Matzke. Plant Physiology. 1995. vol. 679–685.
Itoh et al. Mol Gen Genet. 1997. 255: 351–358.
Finnegan and McElroy. Bio/Technology. 12: 883–888, 1994.
Heck etal. The Plant Cell. 7: 127111–1282, 1995.
Perry et al. The Plant Cell. 1996. 8: 1977–1989.
Valvekens et al. Proc. Natl. Acad. Sci. USA. 1988. 85: 5536–5540.
Heck, Gregory R., et al., "AGL15, a MADS Domain Protein Expressed in Developing Embryos," *The Plant Cell*, 7:1271–1282 (Aug. 1995).
Perry, Sharyn E., et al., "The MADS Domain Protein AGL15 Localizes to the Nucleus during Early Stages of Seed Development," *The Plant Cell*, 8:1977–1989 (Nov. 1996).
Rousley, Steven D., et al., "Diverse Roles for MADS Box Genes in Arabidopsis Development," *The Plant Cell*, 7:1259–1269 (Aug. 1995).
C. Flanagan and H. Ma, "Spatially and temporally regulated expression of the MADS–box gene AGL2 in wild–type and mutant arabidopsis flowers", *Plant Molecular Biology*, 26, 581–595 (Oct. 1994).

*Primary Examiner*—Gary Benzion
*Assistant Examiner*—Ousama Zaghmout

[57] ABSTRACT

A transgenic flowering plant exhibiting a novel phenotype contains in its genome a genetic construct in which an AGL15 sequence is placed under the control of a promoter that is expressed in the plant, the promoter not being natively associated with the AGL15 sequence. A genetic construct that is useful for obtaining transgenic plants includes an AGL15 sequence under the control of a promoter, not natively associated with the AGL15 sequence, which is functional in plants.

28 Claims, 1 Drawing Sheet

DF164

DF121

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
        (A) LENGTH: 1070 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:1:

```
GTTCAATTTT GGGGGAAAAT GGGTCGTGGA AAAATCGAGA TAAAGAGGAT CGAGAATGCG      60

AATAGCAGAC AAGTCACTTT TTCCAAGAGG CGTTCTGGGT TACTTAAGAA AGCTCGTGAG     120

CTCTCTGTTC TTTGTGATGC TGAAGTTGCT GTCATCGTCT TCTCTAAGTC TGGCAAGCTC     180

TTCGAGTACT CCAGTACTGG AATGAAGCAA ACACTTTCCA GATACGGTAA TCACCAGAGT     240

TCTTCAGCTT CTAAAGCAGA GGAGGATTGT GCAGAGGTGG ATATTTTAAA GGATCAACTT     300

TCAAAGCTTC AAGAGAAACA TTTACAACTG CAGGGCAAGG GCTTGAATCC TCTGACCTTT     360

AAAGAGCTGC AAAGCCTTGA GCAGCAACTA TATCATGCAT TGATTACTGT CAGAGAGCGA     420

AAGGAACGAT TGCTGACTAA CCAACTTGAA GAATCACGCC TCAAGGAACA ACGAGCAGAG     480

TTGGAAAACG AGACCTTGCG TAGACAGGTT CAAGAACTGA GGAGCTTTCT CCCGTCGTTC     540

ACCCACTATG TTCCATCCTA CATCAAATGC TTTGCTATAG ATCCAAAGAA CGCTCTCATA     600

AACCACGACA GTAAATGCAG CCTCCAGAAC ACCGATTCAG ACACAACTTT GCAATTAGGG     660

TTGCCGGGAG AGGCACATGA TAGAAGGACG AATGAAGGAG AAAGAGAGAG CCCGTCAAGC     720

GATTCAGTGA CAACAAACAC GAGCAGCGAA ACTGCAGAAA GAGGGGATCA GTCTAGTTTA     780

GCAAATTCTC CACCTGAAGC CAAAAGACAA AGGTTCTCTG TTTAGTCCTA GAAAAGTATG     840

GGAGAAGGCT ACTAATGTTT CCTCTTTAGC AGTATCCGAT TGTTTTAAAA GTAATTTTAG     900

AGGGATACTT GCAAAAAGAA GAGAAGATTC AGTTATCTAA TCTCTGCACC AACTCTCTTT     960

GTCCTTCTTC TTTTGATTAT TTCTCGACTG TCTCTCCTAT AAAAAAGATA TGCCTAGCTG    1020

AGAGTTTGAA ATCCATAATC TTTACAAGGC ACAGAGTTAT TTGACAAAAA               1070
```

(2) INFORMATION FOR SEQ ID NO:2:

(i) SEQUENCE CHARACTERISTICS:
        (A) LENGTH: 795 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
ATGGGTCGTG GAAAAATTGA GATAAAGAGG ATCGAGAATG CGAATAGCAG GCAAGTTACC      60

TTCTCCAAGA GGCGTGCTGG TTTGCTCAAG AAAGCTCATG AGCTCTCTGT TCTTTGTGAC     120

GCTGAGGTTG CCGTCATTGT CTTCTCCAAG TCTGGCAAGC TCTTCGAGTT CTCAAGTACT     180

AGCATGAAGA AAACACTTTT GAGATACGGA AATTATCAGA TCTCTTCAGA TGTTCCTGGG     240

ATTAACTGTA AAACAGAGAA CCAGGAGGAG TGTACAGAGG TGGACCTTTT AAAGGATGAG     300

ATCTCAATGC TTCAAGAGAA ACATTTACAC ATGCAGGGTA AGCCCTTGAA CCTTCTGAGC     360

TTGAAAGAGC TGCAACACCT TGAGAAGCAA CTAAATTTCT CATTGATATC TGTGAGAGAG     420

CGAAAGGAAC TATTGTTGAC TAAACAACTT GAAGAGTCAC GGCTTAAGGA ACAGAGAGCA     480

GAGCTGGAAA ACGAGACCTT ACGTAGACAG GTTCAAGAAC TAAGGAGTTT TCTCCCGTCG     540

ATCAACCAAC ACTATGCTCC ATCCTACATC AGATGCTTCG CTATAGATCC TAAGAACTCA     600

CTCTTAAGCA ACACTTGCTT GGGCGACATT AACTGCAGCC TCCAGAACAC CAACTCAGAC     660

ACAACTTTGC AACTAGGGTT GCCGGGAGAA GCACATGATA CAAGGAAGAA CGAAGGAGAC     720

AGAGAGAGCC CATCAAGTGA TTCTGTGACA ACGAGCACAA CCAGAGCAAC TGCACAAAGG     780

ATCAGTCTAG TTTAG                                                     795
```

(2) INFORMATION FOR SEQ ID NO:3:

(i) SEQUENCE CHARACTERISTICS:
        (A) LENGTH: 264 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Gly Arg Gly Lys Ile Glu Ile Lys Arg Ile Glu Asn Ala Asn Ser
  1               5                  10                  15

Arg Gln Val Thr Phe Ser Lys Arg Arg Ala Gly Leu Leu Lys Lys Ala
                 20                  25                  30

His Glu Leu Ser Val Leu Cys Asp Ala Glu Val Ala Val Ile Gly Phe
             35                  40                  45

Ser Lys Ser Gly Lys Leu Phe Glu Phe Ser Ser Thr Ser Met Lys Lys
 50                  55                  60

Thr Leu Leu Arg Tyr Gly Asn Tyr Gln Ile Ser Ser Asp Val Pro Gly
 65                  70                  75                  80

Ile Asn Cys Lys Thr Glu Asn Gln Glu Glu Cys Thr Glu Val Asp Leu
                 85                  90                  95

Leu Lys Asp Glu Ile Ser Met Leu Gln Glu Lys His Leu His Met Gln
            100                 105                 110

Gly Lys Pro Leu Asn Leu Leu Ser Leu Lys Glu Leu Gln His Leu Glu
        115                 120                 125

Lys Gln Leu Asn Phe Ser Leu Ile Ser Val Arg Glu Arg Lys Glu Leu
    130                 135                 140

Leu Leu Thr Lys Gln Leu Glu Glu Ser Arg Leu Lys Glu Gln Arg Ala
145                 150                 155                 160

Glu Leu Glu Asn Glu Thr Leu Arg Arg Gln Val Gln Glu Leu Arg Ser
                165                 170                 175

Phe Leu Pro Ser Ile Asn Gln His Tyr Ala Pro Ser Tyr Ile Arg Cys
            180                 185                 190
```

```
Phe Ala Ile Asp Pro Lys Asn Ser Leu Leu Ser Asn Thr Cys Leu Gly
        195                 200                 205

Asp Ile Asn Cys Ser Leu Gln Asn Thr Asn Ser Asp Thr Thr Leu Gln
210                 215                 220

Leu Gly Leu Pro Gly Glu Ala His Asp Thr Arg Lys Asn Glu Gly Asp
225                 230                 235                 240

Arg Glu Ser Pro Ser Ser Asp Ser Val Thr Thr Ser Thr Thr Arg Ala
                245                 250                 255

Thr Ala Gln Arg Ile Ser Leu Val
        260

(2) INFORMATION FOR SEQ ID NO:4:

(i) SEQUENCE CHARACTERISTICS:
        (A) LENGTH: 2679 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:4:
```

| | | | | | |
|---|---|---|---|---|---|
| AAGCTTTGGT | TGTACGGGTC | AAAGTATTCG | TTCTGGGGTG | GAGTTGGAGA | AGCCTTCAGA | 60 |
| GCCAGTTTAG | TAAGGGTTCT | TCGAGGGAGG | TCTGTATAGA | AAGTAGCAAG | CAGAACATGT | 120 |
| TGGCCTTGTC | TAATGTAGAT | AGTTGTAATC | AGTGGTGCTA | CAATGTTGTC | TGATGGAATT | 180 |
| AAATTTCTAA | ATGGTCAAAA | TGAAAACGTT | GAAGAAAAAA | AAAACAATTG | TGATATGATG | 240 |
| ATCTTCCTAC | TTATATCATA | TGATCTGCAC | GGATTAGAAT | TGTGTTTGAG | AGTATATGAT | 300 |
| CTGGATTCTT | TGTTCGTTTA | AATTTCTGAG | TCATTTCAAA | ATCATATTTT | CCTTCGTTGA | 360 |
| TAAAATTATG | TGTTCACTTT | TTCTAGCTCT | GTACAAAAAT | CAATCAACTG | ATTTGTTATT | 420 |
| TGTATAGTTA | TTTGTTTTTT | ACCAAGTCTT | GCTCTGATTT | TTTTTTTTTA | GTCTTGCTCT | 480 |
| GATTTATACC | ATCAACATCA | AGTACATTTT | TTCGTGGTCA | AACATCAAGT | ACAATTTTTA | 540 |
| TATTAGCGTA | AACAAATATA | AAGAAATATT | GTTTTTGTCG | GCAGAATAAA | AGAAATATAA | 600 |
| AAAGCAATTG | GTAAAGCAAT | AATAACTTTT | TTAAAACAGT | GGAAAAAAGA | AGAAGAATCT | 660 |
| CAACTGTTAT | GGCAACAAAA | GGAAACGTGG | GTCCCAGAGG | AACTGGCAAA | CCCTCTAAAT | 720 |
| GTGGCAAAAA | GGTGTCATGC | AAATACTCTA | AAAGAGAGAG | AGAGAGGAGC | ACGCAAAACA | 780 |
| GTGCTCATGC | AAACACAAAC | ACAGTTAAGT | TTCTTTGTAG | TTTGTACTAA | TCTCTCTTTT | 840 |
| TTATATATAT | ATTACATCCA | AATATAGCAA | ATCTTTGTGT | CTTCCTTTTA | TAGATTGTAA | 900 |
| CCCCAAAAAG | GAGTTTCAAT | AGGGAAGAAG | AGAGATTGAA | ACTCCTTTTC | TTTCTTCATC | 960 |
| TTCTTTTTTC | TCTTCTGTGC | TTGAAGATGG | GTCGTGGAAA | AATTGAGATA | AAGAGGATCG | 1020 |
| AGAATGCGAA | TAGCAGGCAA | GTTACCTTCT | CCAAGAGGCG | TGCTGGTTTG | CTCAAGAAAG | 1080 |
| CTCATGAGCT | CTCTGTTCTT | TGTGACGCTG | AGGTTGCCGT | CATTGTCTTC | TCCAAGTCTG | 1140 |
| GCAAGCTCTT | CGAGTTCTCA | AGTACTAGGG | GGTAATTAAT | CAATCATTTT | CTTGATTCCA | 1200 |
| TTTTCCTTTT | TGCATGTCTA | CGTTTGATGG | CTTCTGAGAG | TTAAGATGTG | TTTGCTCTTG | 1260 |
| GTTAACCTGG | TTCTTGCATG | TTTGTTTAGA | TTCATTAGTC | CTAATTAATC | TCACATTTGC | 1320 |
| TTCTTAGATC | TAATTTCTCA | TTTGGTTTTC | AGCATGAAGA | AAACACTTTT | GAGATACGGA | 1380 |
| AATTATCAGA | TCTCTTCAGA | TGTTCCTGGG | ATTAACTGTA | AAACAGAGGT | TAGAAACTCA | 1440 |
| TGTGGTTTTT | GCCTAGACTC | AACTCAAGTG | TTTTTGACTG | TTTTGTCTCG | ATGCATCAAA | 1500 |
| ACTTTGTTTA | GAACCAGGAG | GAGTGTACAG | AGGTGGACCT | TTTAAAGGAT | GAGATCTCAA | 1560 |

```
TGCTTCAAGA GAAACATTTG TATGGAACCC AATCCTAATT TATATTATTT TTTCCCCACA    1620

CCATCCACCA CTTTTGTGTG TCTTATATGG TTTGTCTTTG TGTGTGTTTG TAGACACATG    1680

CAGGGTAAGC CCTTGAACCT TCTGAGCTTG AAAGAGCTGC AACACCTTGA GAAGCAACTA    1740

AATTTCTCAT TGATATCTGT GAGAGAGCGA AAGGTAAAAA ACTAGTAATA TCACTCTTCC    1800

CCATTTCTTT TCTCATTAAA AACATATTTG CATTTTTCTG AATAAAAGTT TATGTGATTT    1860

CAGGAACTAT TGTTGACTAA ACAACTTGAA GAGTCACGGC TTAAGGTAAC TCTTGAGTTA    1920

TATGAAACAC TTGATTTTTT CTGATTAGCT TCTAAGCATG CAAGATTATG TGATCACATG    1980

ATTCTGATGA ACCGTTTTAA AAATGTATGT CCCCTCTTTA CTGCCTATTG TATCCTTTGA    2040

GAGGGTTCAT GTTGTAGCTA GCTATCTTAA CTGAGTATGA TGCAATAGTT GATCATCTAG    2100

AGCATTGAAA CTCTGCAGGA ACAGAGAGCA GAGCTGGAAA ACGAGACCTT ACGTAGACAG    2160

GTGACGAAAC CATTCTTATA ATTTGTGTTG TATCATCTCT TATCACCAAG TCTTCTTTTT    2220

ACTACTTCTA ATCAGCTTCT CTTGAAAATA GGTTCAAGAA CTAAGGAGTT TTCTCCCGTC    2280

GATCAACCAA CACTATGCTC CATCCTACAT CAGATGCTTC GCTATAGATC CTAAGAACTC    2340

ACTCTTAAGC AACACTTGCT TGGGCGACAT TAACTGCAGC CTCCAGAACA CCAACTCAGA    2400

CACAACTTTG CAACTAGGGT ATGTGCTCTT TTAACTCTTT TTGCTACCAT TGGTTGCACT    2460

ATAGTTAGCC AAAAGTACTC TTCTAGTATA CATATGCATT AACACTATTG GACTTATTAA    2520

TTCTCACATG TGTTGTTTTC TTGAAGGTTG CCGGGAGAAG CACATGATAC AAGGAAGAAC    2580

GAAGGAGACA GAGAGAGCCC ATCAAGTGAT TCTGTGACAA CGAGCACAAC CAGAGCAACT    2640

GCACAAAGGA TCAGTCTAGT TTAGAAACTA TTTCATCTG                          2679

(2) INFORMATION FOR SEQ ID NO:5:

(i) SEQUENCE CHARACTERISTICS:
        (A) LENGTH: 951 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:5:

GAGATAAAGA GGATCGAGAA TGCGAATAGC AGACAAGTTA CTTTCTCCAA GAGGCGTGCT      60

GGTTTGCTCA AGAAGGCTCA TGAGCTCTCT GTTCTTTGCG ACTCTGAGGT TGCCGTCATC     120

GTCTTCTCCA AGTCCGGCAA GCTCTTCGAG TTCTCAAGTA CTGGCATGAA GCGAACCGTT     180

TTGAGATACG AGAACTACCA ACGTTCTTCA GATGCTCCTC TGATTAAATA TAAACCAGAG     240

AACCAGGAGG AGGATTGTAC AGAGGTGGAC TTTTTAAAGA ATGAGATCTC AAAGCTTCAA     300

GAGAAACATT TACAAATGCA AGGTAAGGGC TTGAATGCTC TGTGCTTGAA AGAGCTGCAA     360

CACCTTGAAC AGCAACTAAA TGTCTCGTTG ATATCTGTGA GAGCGAAA GAACTATTG       420

TTGACTAAAC AAATTGAAGA ATCACGTATC AGGGAACAGA GAGCAGAGCT GGAAAACGAG     480

ACCTTACGTA GACAGGTTCA AGAACTTAGA AATTTTCTCC CGTCCATCAA CCAAAACTAT     540

GTTCCATCCT ACATCACATG CTTCGCTATA GATCCCAAGA ACTCCCCCGT GAACAACTCT     600

GGCTTGGACG ACACTAATTA CAGTCTCCAG AAGACCAATT CAGACACAAC ATTGCAGTTG     660

GGGTTGCCGG GAGAAGCACA GGCTAGAAGG AGGAGTGAAG CAAATAGAGA GAGCCCATCA     720

AGTGATTCAG TAACAACGAG CACCACCAAA GCAACTCCAC AAAGGATCAA TCTAGTTTAG     780

CACCTGAAAA CAAAAGCAAA TGGTTCTCTG CTTAGCCACA TAGAAATATG GGAATGAGGC     840

ACATGATGTT TTCCTCTGTA GCAAGTATCA CATTATTTCA AAACCAATGT TAGAAGAGAT     900
```

```
GAATCCGATG TATCTCATCT CACATTCTAG TCTAACTCTA ACCCCACTCT T              951
```

(2) INFORMATION FOR SEQ ID NO:6:

(i) SEQUENCE CHARACTERISTICS:
        (A) LENGTH: 2437 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

```
ATCAACAATG CTAGTTGTTG CATTTTATTC TTGGGGTACT TTGAAATTGT TTCTAATTGT       60

TGCTCTGAAC TTTTTTATTT TATGTCGGTC AACATTGTTG CTCTGATTTA TGTCTTACAA      120

CAACATTAAA GAGAAAATAC ACTAGTACTA ATAAATCTAA TTTTAAAGAG AAGGAAAAAA      180

GAGGAAAGAA AAAACAACT TTAGGAAGAA AAGGGAAAGT AGGACCCAGA AGAACTGACA       240

AAATCCTCCA AATGTGGCAA AAAGGTATCA TGCAAAAAAC CCTAAAATTG AAAAAAGAGA     300

GCACGCAAAA CAGTGGCCAT GCAACACACA ATATTCATTA CCGAGTTTTT ACCTTTCTTT     360

CTTTTTTCTA TAAAAAAAAA AATATTCCAT CCAAATTTAG CAATCTTTTG TGTTCCCATT     420

AATAGATTCC CAAAAAGCAC TTCTAAACCC ATTTTGGAAT ACATTGAACC TTTCCTCTTC     480

TTCTTCTTCC TTCTACCTTC TTCTCTCTGT TCAATTTTGG GGGAAAATGG GTCGTGGAAA     540

AATCGAGATA AAGAGGATCG AGAATGCGAA TAGCAGACAA GTCACTTTTT CCAAGAGGCG     600

TTCTGGGTTA CTTAAGAAAG CTCGTGAGCT CTCTGTTCTT TGTGATGCTG AAGTTGCTGT     660

CATCGTCTTC TCTAAGTCTG GCAAGCTCTT CGAGTACTCC AGTACTGGGT AACACTTATT     720

TCTTTTTGAT TCAATTTTGG TTTTGCATGT CTTGTCTTGT TGTGATTAGA ATCGATTTCG     780

GGAACTGTAA TTGATTTTTG TTTTTGCATG TTTGTTAAGA TTAAAAGTTT TCTGATTGAG     840

CTGAAGAGAG TCCTAATTTT GAATTCTCAT TTGATTTTAG AATGAAGCAA ACACTTTCCA     900

GATACGGTAA TCACCAGAGT TCTTCAGCTT CTAAAGCAGA GGTGAGAATC ATTCATTCTT     960

GTCTCATATA TCTTGAAATT GTTTTTTTGA AAATCTGATT GCTGTTTAGA ACCTCCAGGA    1020

GGATTGTGCA GAGGTGGATA TTTTAAAGGA TCAACTTTCA AAGCTTCAAG AGAAACATTT    1080

GTATGGAAAC TAAATAAATC TCACTATGCT TGTTCATTAC TTTATTCTTC TCTACTTTGT    1140

GTTTGTTTAT ATTGTTTGGC TTTGTGTGTT CTGTTCTGTT GTAGCAACT GCAGGGCAAG     1200

GGCTTGAATC CTCTGACCTT TAAAGAGCTG CAAAGCCTTG AGCAGCAACT ATATCATGCA    1260

TTGATTACTG TCAGAGAGCG AAAGGTAACT AGTAATATCA CTCTTCCATC ATCATTTCTC    1320

TTTGCATTGT CCTGATTATG GTTATCTGAT TTCAGGAACG ATTGCTGACT AACCAACTTG    1380

AAGAATCACG CCTCAAGGTA AACACTAGCT TTTCCTCTCT AGCTTCCAAA TGTAAGCTTA    1440

TGTGTAATCA CATGATTCTG AACCTTGTTA AAACCAGTGG CTATCCTTTG ACAAGCTCAT    1500

GCTCTAACTA GCTAGTGTGC AGTTTATTTG TCTTAAGACT CCTATATAAC TAGGTACAGA    1560

GTACAAAAGT ATAATTTCTT GATTAGCCAT ATATATACTT TGCAGGAACA ACGAGCAGAG    1620

TTGGAAAACG AGACCTTGCG TAGACAGGTT CTTATTATTT TTGTTGAATC ATCTCCTAAT    1680

GAACGCTTCT TCCTCTGACT TGTAATTACT TGTTGAAACA GGTTCAAGAA CTGAGGAGCT    1740

TTCTCCCGTC GTTCACCCAC TATGTTCCAT CCTACATCAA ATGCTTTGCT ATAGATCCAA    1800
```

```
AGAACGCTCT CATAAACCAC GACAGTAAAT GCAGCCTCCA GAACACCGAT TCAGACACAA    1860

CTTTGCAATT AGGGTATTGC TCTTTTAAGT CTATTTGCTG TCATTGGTTG CATTATTGGA    1920

AAGCTGATTT AAGATAAATA TAAGTCTTTT TCCTCCTCTG TTAGTTATGC ATATGCCTTA    1980

ACACTCACTA ACTGGTGTTA TAAAATTCTT ACTACTTGTG TTTTCTCCAA GGTTGCCGGG    2040

AGAGGCACAT GATAGAAGGA CGAATGAAGG AGAAAGAGAG AGCCCGTCAA GCGATTCAGT    2100

GACAACAAAC ACGAGCAGCG AAACTGCAGA AGAGGGGAT CAGTCTAGTT TAGCAAATTC     2160

TCCACCTGAA GCCAAAAGAC AAAGGTTCTC TGTTTAGTCC TAGAAAAGTA TGGGAGAAGG    2220

CTACTAATGT TTCCTCTTTA GCAGTATCCG ATTGTTTTAA AAGTAATTTT AGAGGGATAC    2280

TTGCAAAAAG AAGAGAAGAT TCAGTTATCT AATCTCTGCA CCAACTCTCT TTGTCCTTCT    2340

TCTTTTGATT ATTTCTCGAC TGTCTCTCCT ATAAAAAAGA TATGCCTAGC TGAGAGTTTG    2400

AAATCCATAA TCTTTACAAG GCACAGAGTT ATTTGAC                             2437
```

(2) INFORMATION FOR SEQ ID NO:7:

(i) SEQUENCE CHARACTERISTICS:
        (A) LENGTH: 268 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:7:

```
Met Gly Arg Gly Lys Ile Glu Ile Lys Arg Ile Glu Asn Ala Asn Ser
 1               5                  10                  15

Arg Gln Val Thr Phe Ser Lys Arg Arg Ser Gly Leu Leu Lys Lys Ala
            20                  25                  30

Arg Glu Leu Ser Val Leu Cys Asp Ala Glu Val Ala Val Ile Val Phe
        35                  40                  45

Ser Lys Ser Gly Lys Leu Phe Glu Tyr Ser Ser Thr Gly Met Lys Gln
    50                  55                  60

Thr Leu Ser Arg Tyr Gly Asn His Gln Ser Ser Ala Ser Lys Ala
65                  70                  75                  80

Glu Glu Asp Cys Ala Glu Val Asp Ile Leu Lys Asp Gln Leu Ser Lys
                85                  90                  95

Leu Gln Glu Lys His Leu Gln Leu Gln Gly Lys Gly Leu Asn Pro Leu
            100                 105                 110

Thr Phe Lys Glu Leu Gln Ser Leu Glu Gln Gln Leu Tyr His Ala Leu
        115                 120                 125

Ile Thr Val Arg Glu Arg Lys Glu Arg Leu Leu Thr Asn Gln Leu Glu
    130                 135                 140

Glu Ser Arg Leu Lys Glu Gln Arg Ala Glu Leu Glu Asn Glu Thr Leu
145                 150                 155                 160

Arg Arg Gln Val Gln Glu Leu Arg Ser Phe Leu Pro Ser Phe Thr His
                165                 170                 175

Tyr Val Pro Ser Tyr Ile Lys Cys Phe Ala Ile Asp Pro Lys Asn Ala
            180                 185                 190

Leu Ile Asn His Asp Ser Lys Cys Ser Leu Gln Asn Thr Asp Ser Asp
        195                 200                 205

Thr Thr Leu Gln Leu Gly Leu Pro Gly Glu Ala His Asp Arg Arg Thr
    210                 215                 220

Asn Glu Gly Glu Arg Glu Ser Pro Ser Ser Asp Ser Val Thr Thr Asn
225                 230                 235                 240
```

-continued

```
Thr Ser Ser Glu Thr Ala Glu Arg Gly Asp Gln Ser Ser Leu Ala Asn
            245                 250                 255

Ser Pro Pro Glu Ala Lys Arg Gln Arg Phe Ser Val
            260                 265
```

AGL15 SEQUENCES IN TRANSGENIC PLANTS

CROSS-REFERENCE TO RELATED APPLICATIONS

This application claims priority from provisional application Ser. No. 60/031,205 filed Nov. 21, 1996.

STATEMENT REGARDING FEDERALLY SPONSORED RESEARCH OR DEVELOPMENT

This invention was made with United States Government support through NSF grant # DCB-9105527, NSF Postdoctoral Research Fellowship grant # BIR-9403929 awarded to Sharyn E. Perry, and grant # BIR-92020331 from the DOE/NSF/USDA Collaborative Program on Research in Plant Biology Training Program. The United States Government has certain rights in this invention.

BACKGROUND OF THE INVENTION

Modern biotechnology has devoted considerable effort to the development of phenotypically distinct plants with economically advantageous qualities. Valuable features in food crops include increased yields, extended shelf-life, and delayed fruit ripening that is susceptible to external control. In the floral industry, there is interest in delaying senescence of both cut and uncut flowers.

Efforts to develop crop plants that produce higher yields have been directed toward pest control or toward the selection and breeding of varieties that bear greater numbers of fruits, or that produce larger fruits. These crop breeding endeavors are very time-consuming and labor-intensive, and have not resulted in dramatically increased crop yields.

Much of the research on senescence in plants has focused on the manipulation of the plant hormone cytokinin, because there is evidence that suggests an inverse correlation between levels of the plant hormone cytokinin and the onset of senescence. Plant varieties with high levels of endogenous cytokinin tend to have blooms that are longer lived. The application of cytokinin to blooms or to the holding solution of cut flowers has been tested as a means for extending flower longevity. The success of this method is equivocal, and plant response to cytokinins is affected by numerous parameters, some of which are immutable.

One of the means by which cytokinin is thought to delay floral senescence is by decreasing the sensitivity of floral tissues to ethylene and/or interfering with the production of ethylene. Increased levels of ethylene are correlated with accelerated senescence in petals. Experiments designed to manipulate ethylene levels were conducted using transgenic carnations that contained a construct directing expression of an antisense RNA complementary to the mRNA of ACC synthase, an enzyme involved in the biosynthesis of ethylene. The results of that research did not conclusively demonstrate delayed senescence in flowers of transgenic carnations in which the antisense RNA was expressed.

In fruits, high levels of cytokinins are associated with delayed ripening, but not delayed senescence. The exogenous application of cytokinins to ripening fruit has been employed to delay ripening. U.S. Pat. No. 5,177,307 describes the manipulation of cytokinins in transgenic tomato plants containing a construct that directs the tissue-specific expression of an enzyme involved in the biosynthesis of cytokinin. These transgenic tomato plants exhibit increased expression of cytokinins, and produce fruit with a blotchy appearance.

Tillable land available for production of food crops continues to diminish because each year, more acreage is devoted to alternative uses. At the same time, the human population is rapidly increasing. Therefore, it is essential to increase agricultural productivity to meet the nutritional needs of the world's burgeoning population.

Within the floral and landscaping industries, producers, florists, and professional gardeners and landscapers are desirous of methods for increasing the number and persistance of blooms on ornamental flowering plants and cut flowers. Human enjoyment of ornamental flowering plants and cut flowers can be enhanced by extending the longevity of the flowers.

BRIEF SUMMARY OF THE INVENTION

The present invention is a transgenic flowering plant comprising in its genome a genetic construct comprising an AGL15 (AGL for AGAMOUS-like) DNA sequence and a promoter, not natively associated with the AGL15 sequence, that promotes expression of the AGL15 sequence in the plant.

The present invention is also a plant cell, derived from a flowering plant, comprising in its genome a genetic construct comprising an AGL15 DNA sequence and a promoter, not natively associated with the AGL15 sequence, that promotes gene expression in plants.

The present invention is also a seed, derived from a flowering plant, comprising in its genome a genetic construct comprising an AGL15 DNA sequence and a promoter, not natively associated with the AGL15 sequence, that promotes gene expression in plants.

The present invention is also a genetic construct comprising an AGL15 DNA sequence and a promoter, not natively associated with the AGL15 sequence, that promotes expression of the AGL15 sequence in plants.

It is an object of the present invention to provide a transgenic flowering plant that has a novel phenotype with advantageous properties.

It is another object of the present invention to provide transgenic seed from flowering plants.

It is an object of the present invention to provide a genetic construct comprising an AGL15 sequence and a promoter, not natively associated with the AGL15 sequence and which promotes expression of AGL15 in plants at levels that result in novel phenotypes.

Other objects, advantages, and features of the present invention will become apparent after review of the specification, drawings, and claims.

DETAILED DESCRIPTION OF THE INVENTION

Figure 1A:
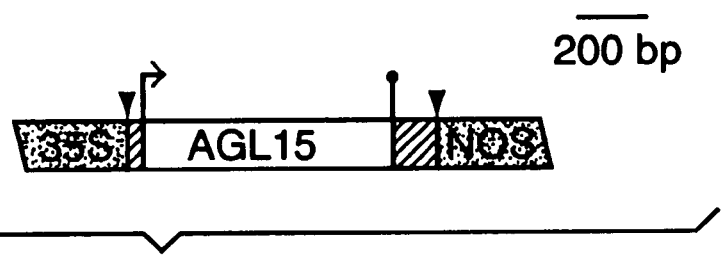
FIG. 1A is a schematic map of a genetic construct, designated DF164, which contains the cauliflower mosaic virus 35S promoter (35S), an Arabidopsis AGL15 cDNA fragment (SEQ ID NO:1) comprising an 18-bp 5' untranslated region (UTR), an 807-bp open reading frame (ORF), a 245-bp 3' UTR, and a nopaline synthetase terminator (NOS). The inverted triangles demark the AGL15 cDNA fragment; the crosshatched regions indicate the 5' and 3' UTRs; the white region denotes the AGL15 ORF; the arrow indicates the translational start site and the direction in which the sequence is read.

One aspect of the present invention is a transgenic flowering plant that contains in its genome a genetic construct comprising an AGL15 DNA sequence and a promoter, not natively associated with the AGL15 sequence, which promotes expression of the AGL15 in the transgenic flowering plant.

As an example of the efficacy of this invention, transgenic Arabidopsis plants that contain a genetic construct comprising an AGL15 sequence under the control of the cauliflower mosaic virus 35S promoter (CaMV 35S) have been developed as detailed in the examples below. Arabidopsis plants in which the recombinant AGL15 sequence is expressed exhibit unique phenotypes, characterized by a number of advantageous qualities, including increased numbers of flowers and fruits, delayed maturation of fruit, delayed floral organ senescence and abscission, and delayed senescence of cut flowers and inflorescences.

As the examples below demonstrate, AGL15 sequences are ubiquitous and highly conserved among angiosperm plant species. It is therefore expected that any flowering plant can be used in the practice of the present invention. For example, a flowering plant that produces edible fruit may be used. The flowering plant could also be a plant whose flowers are valued for their ornamental properties. The present invention could be practiced using a flowering plant that is raised for its production of seed, flowers, or fruit.

Transgenic Arabidopsis plants were obtained using the Agrobacterium transformation system, as described in the examples. Agrobacterium-mediated transformation is known to work well with all dicot plants and some monocots. Other methods of transformation equally useful in dicots and monocots may also be used in the practice of the present invention. Transgenic plants may be obtained by particle bombardment, electroporation, or by any other method of transforming plants known to one skilled in the art of plant molecular biology. The experience to date in the technology of plant genetic engineering is that the method of gene introduction is not of particular importance in the phenotype achieved in the transgenic plants.

A transgenic plant may be obtained directly by transformation of a plant cell in culture and regeneration of a plant. More practically, transgenic plants may be obtained from transgenic seeds set by parental transgenic plants. Transgenic plants pass on inserted genes, sometimes referred to as transgenes, to their progeny by normal Mendellian inheritance just as they do their native genes. Methods for breeding and regenerating plants of agronomic interest are known in the art.

Two AGL15 sequences derived from Arabidopsis have been found to be useful in the practice of the present invention. One useful sequence is an Arabidopsis AGL15 cDNA sequence (SEQ ID NO:1) that has been isolated and characterized as described in detail in the examples. Briefly, the Arabidopsis AGL15 cDNA was derived from mRNA that is preferentially expressed during embryogenesis. A second useful Arabidopsis AGL15 sequence was made by genetically engineering the cDNA sequence of SEQ ID NO:1 to include three introns from the sole Arabidopsis genomic AGL15 gene sequence, which was isolated as descibed below.

The examples below demonstrate that other plants contain sequences that are homologous to the AGL15 sequence of Arabidopsis. Two *Brassica napus* AGL15 cDNA sequences and one genomic sequence have been identified and characterized as described in the examples below. DNA sequence analysis revealed that these sequences are highly homologous to the Arabidopsis AGL15 gene.

Numerous genera of flowering plants were examined and found to produce a protein product that binds antibodies raised against an AGL15-specific polypeptide.

By "AGL15 sequence" it is meant a DNA sequence sufficiently homologous to SEQ ID NO:1 to exhibit AGL15 activity when expressed in a transgenic plant under the control of a promoter functional in that plant. An AGL15 sequence may be an unmodified sequence isolated from any flowering plant, a cDNA sequence derived from mRNA preferentially expressed during embryogenesis, a cDNA sequence engineered to include introns, a sequence that is modified in vitro to contain a sequence distinct from that of a naturally occurring sequence, a heterologous sequence that is constructed in vitro, or a sequence that is synthesized in vitro.

By "AGL15 activity" it is meant the occurrence of a novel phenotype, characterized by increased numbers of flowers and fruits, delayed maturation of fruit, delayed floral organ senescence and abscission, or delayed senescence of cut flowers and inflorescences, which correlates with the expression of an AGL15 sequence in a transgenic plant comprising in its genome the AGL15 sequence under the control of a functional promoter that is not natively associated with the AGL15 sequence.

Because AGL15 sequences are highly conserved among flowering plants, it is reasonably anticipated that an AGL15 sequence from any flowering plant may be used in the practice of the present invention. To identify potential AGL15 sequences, which are preferentially expressed during embyryogenesis, an AGL15-specific region of an AGL15 sequence may be used to probe a cDNA library made from plant embryos. Another approach to identifying AGL15 sequences employs PCR amplification using AGL15-specific degenerate primers. In addition, AGL15 sequences may be identified in a plant genomic library using an AGL15-specific probe.

Sequences homologous to AGL15-specific sequences from Arabidopsis have been found in numerous species of flowering plants. It anticipated that these sequences have AGL15 activity, even if they do not exhibit complete sequence identity with SEQ ID NO:1. It is expected that polyploid plants having more than one copy of the AGL15 gene may have allelic variations among AGL15 gene sequences. It is anticipated that putative AGL15 sequences having less than 100% sequence homology to the sequence shown in SEQ ID NO:1 will exhibit AGL15 activity.

It is envisioned that minor sequence variations from SEQ ID NO:1 associated with nucleotide additions, deletions, and mutations, whether naturally occurring or introduced in vitro, will not affect AGL15 activity. The scope of the present invention is intended to encompass minor variations in AGL15 sequences.

It is anticipated that a region of an AGL15 cDNA sequence may be used to construct a heterologous sequence having AGL15 activity using methods known in the art of molecular biology. This may be accomplished by ligating an AGL15-specific region of an AGL15 sequence to a DNA sequence that encodes a protein that lacks AGL15 activity, but which has domains that are functionally analogous to domains encoded by nonAGL15-specific regions of an AGL15 sequence.

By an "AGL15-specific sequence", it is meant a DNA sequence that is common to all putative AGL15 sequences and which is distinct from sequences common to both AGL15 and related protein-coding sequences that lack AGL15 activity. Characterization of protein domains encoded by AGL15 sequences is discussed in detail in the examples. Briefly, an AGL15 protein contains a domain that is unique to AGL15, as well domains that are common to many related proteins not known to possess AGL15 activity. The sequence comprising bases 190–1060 of SEQ ID NO:1 is an example of an AGL15-specific sequence.

Figure 1B:
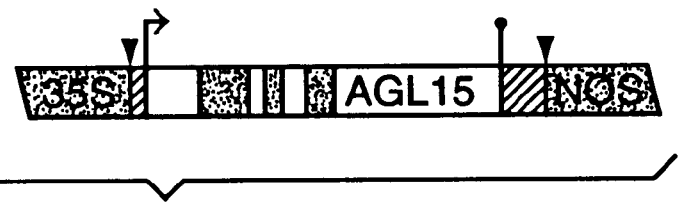
FIG. 1B is a schematic map of a genetic construct, designated DF121, which contains the sequence of DF164 and three introns from a genomic Arabidopsis AGL15 gene that were introduced into DF164 by genetic engineering methods known in the art. The symbols and shadings are employed in FIG. 1A have the same meanings in FIG. 1B. Additionally, the solid regions within the ORF denote introns derived from the Arabidopsis genomic AGL15 sequence.

The present invention is also directed toward a genetic construct comprising an AGL15 DNA sequence and a promoter, not natively associated with the DNA sequence, which promotes expression of the AGL15 sequence in plants at levels sufficient to cause novel phenotypes. The creation of two constructs that were found to allow expression of the AGL15 gene at levels sufficient to cause novel phenotypes in Arabidopsis plants that contain one of the constructs is described in detail in the examples. These constructs, designated DF164 and DF121, are shown in FIG. 1A and FIG. 1B. Briefly, relevant features of these constructs include, in 5' to 3' order, the CaMV 35S promoter operably connected to the AGL15 sequence of SEQ ID NO:1, or SEQ ID NO:1 modified to include three genomic introns, the nopaline synthase terminator (NOS), and a gene that encodes a protein that confers kanamycin resistance.

The CaMV 35S promoter is a constituitive promoter known to function in a wide variety of plants. Other promoters that are functional in the plant into which the construct will be introduced may be used to create genetic constructs to be used in the practice of the present invention. These may include other constitutive promoters, tissue-specific promoters, developmental stage-specific promoters, and inducible promoters. Promoters may also contain certain enhancer sequence elements that improve the efficiency of transcription.

The AGL15 sequence used to construct DF164 is an Arabidopsis cDNA sequence that contains a complete ORF, as well as 5' and 3' UTRs. A suitable genetic construct may contain AGL15 cDNA or genomic sequences from other genera of plants. A suitable construct may include a complete AGL15 ORF, with or without a 5' UTR, and with or without a 3' UTR. The length of any UTR that is included in a construct may vary. A suitable construct may include an AGL15-specific subregion of an AGL15 ORF. It is anticipated that a construct that includes an AGL15-specific subregion ligated in-frame to a heterologous sequence that encodes the nonAGL15-specific domains of the AGL15 protein may be used in the practice of the present invention.

The examples below demonstrate that the construct DF121, which contains the Arabidopsis cDNA sequence of SEQ ID NO:1, into which three genomic introns have been engineered, is useful in the practice of the present invention. In general, genomic introns enhance expression of gene sequences. It has also been demonstrated that DF164, a construct containing an AGL15 sequence with no introns, works in the practice of the present invention. It is therefore reasonable to expect that a construct containing an AGL15 sequence with one or two introns may also be used to generate transgenic plants with advantageous features. It is anticipated that a construct containing an AGL15 sequence with more than three introns may be used in the present invention.

The examples below describe the use of an expression vector that contains a kanamycin resistance gene as a selectable marker for selection of plants that have been transformed with the genetic construct. Numerous selectable markers, including antibiotic and herbicide resistance genes, are known in the art of plant molecular biology and may be used to construct expression vectors suitable for the practice of the present invention. Expression vectors may be engineered to include screenable markers, such as beta-glucuronidase (GUS).

The genetic constructs employed in the examples below were engineered using the plasmid vector pBI121 (Clontech). It is anticipated that other plasmid vectors or viral vectors, or other vectors that are known in the art of molecular biology, will be useful in the development of a construct that may be used to transform a plant and allow expression of an AGL15 sequence. We describe the creation of a genetic construct suitable for transformation using the Agrobacterium system. However, any transformation system for obtaining transgenic plants, including particle bombardment, electroporation, or any other method known in the art, may be employed in the practice of the present invention. The construction of vectors and the adaptation of a vector to a particular transformation system are within the ability of one skilled in the art.

The nonlimiting examples that follow are intended to be purely illustrative. Publications cited below are incorporated by reference herein.

EXAMPLES

Isolation and Characterization of AGL15 Sequences

Genes that are preferentially expressed during embryogenesis in *Brassica napus* were identified using the differential display method of Liang and Pardee (*Science* 257:967–971, 1992). Brassica was chosen for initial isolation of sequences prefentially expressed during embyogenesis because of the relatively large size of Brassica embryos. Using the differential display method, mRNA sequences present in developing embryos of *Brassica napus* at the transition and heart stages were compared with mRNA sequences present in older embryos, the post-germination shoot apex, and mature leaves.

One microgram of total RNA from each sample was used in the first strand synthesis reaction. Polymerase chain reaction (PCR) was performed using one-tenth of the first strand cDNA reaction mixture, various primer sets, and 35 S-dATP in 20-ul reactions. After 40 amplification cycles (94° C. for 30 sec, 42° C. for 1 min, and 72° C. for 30 sec), a 4 ul aliquot of the reaction mixture was loaded onto a 6% polyacrylamide sequencing gel. Following electrophoresis, the gel was dried and the differential bands were visualized using autoradiography.

One amplification product, derived from the priming oligonucleotides 5'-$T_{12}$CG-3' and 5'-GAGCTGAAC-3', was present only in samples from developing embryos. This amplification product of approximately 500 bp was recovered by excision of the corresponding band from the dried gel, rehydration of the excised gel band, and electroelution of the cDNA product from the gel. The cDNA was ligated to pBluescript SK- (Stratagene) vector DNA that had been digested with EcoRV and tailed with a single thymidine residue using Taq polymerase. The 500 bp insert was used to screen a cDNA library prepared from transition stage (16–19 days after pollination) *B. napus* embryos. Ten positive clones were identified.

Sequences from several of the ten isolated cDNA clones were analyzed. The full-length Brassica cDNA sequence (SEQ ID NO:2) has an open reading frame of 795 bp and encodes a predicted 30-kD protein of 264 amino acid residues (SEQ ID NO:3). Protein data base comparisons indicate strong homologies to a family of both known and putative transcriptional regulators, known as MADS domain proteins (Schwarz-Sommer et al., Science 250:931–936, 1990). Members of the MADS domain family have been demonstrated to play key roles in critical developmental events in diverse eukaryotic organisms, including yeast, arthropods, vertebrates, and plants.

In general, the MADS domain regulatory proteins possess a MADS domain, which is a highly conserved region of 55–60 amino acid residues that includes a DNA binding domain, a dimerization domain, and a putative phosphorylation site for calmodulin-dependent protein kinases (Sommer et al. EMBO J. 9:605–613, 1990). The MADS domain occurs on the N-terminal region of regulatory protein sequences. Members of the MADS domain family of transcriptional regulators have a second region in common, designated the K domain. The K domains exhibit less conservation of primary sequence but share a putative amphipathic a-helical structure that may be involved in facilitating protein-protein interactions. The C-terminal regions of MADs domain regulatory proteins are divergent.

The *B. napus* MADS domain gene was subsequently designated AGL15 in accordance with the numbering scheme of Rounsley et al. (*Plant Cell* 7:1259–1269, 1995). Because this species of Brassica is tetraploid, it is expected that there is more than one AGL15 locus in the *B. napus* genome. The first cDNA species that was characterized was designated *B. napus* AGL15-1. A genomic AGL15-1 sequence from Brassica was isolated from a genomic library using a probe downstream of the highly conserved MADS domain of the Brassica AGL15-1 cDNA. The sequence of the genomic AGL15-1 sequence from Brassica is shown in SEQ ID NO:4. A second Brassica AGL15 cDNA species, designated AGL15-2, was identified. Its sequence is shown in SEQ ID NO:5.

A homolog of the *B. napus* AGL15-1 in *Arabidopsis thaliana* was identified by probing an Arabidopsis thaliana cDNA library from developing siliques with a sequence from *B. napus* AGL15-1 downstream of the MADS domain. Several full-length cDNA clones were identified. The Arabidopsis homolog of AGL15-1 is shown in SEQ ID NO:1. A region downstream of the MADS domain of the Arabidopsis AGL15 cDNA sequence was used to probe an Arabidopsis genomic library to identify a genomic clone. The DNA sequence of the Arabidopsis genomic AGL15 sequence was determined and is shown in SEQ ID NO:6.

A comparison of the predicted amino acid sequences encoded by the AGL15 cDNA sequences of Brassica (SEQ ID NO:3) and Arabidopsis (SEQ ID NO:7) revealed that the putative transcription factors share 95% amino acid identity in the MADS domain, 71% in the K domain, and 75% in the C-terminal region.

A comparison of protein-coding regions of the AGL15 cDNA sequences from Arabidopsis and Brassica revealed that the Arabidopsis AGL15 cDNA sequence contains an insertion of 4 bases in the C-terminal region. The insertion causes in a frameshift mutation relative to AGL15-1 and the addition of 16 amino acid residues not present in the Brassica protein. Alignment and comparison of the DNA sequences in the C-terminal coding regions of the genes was performed after introducing a four-base gap in the region of AGL15-1 corresponding to the 4-base insertion in the Arabidopsis sequence. This comparison revealed 100% homology between the AGL15 protein-coding sequences of Brassica and Arabidopsis, exclusive of the four-base insert. (Heck et al. *Plant Cell* 7:1271–1282, 1995).

Genomic DNA blot analysis and low-stringency hybridizations suggest that AGL15 represents a single locus in Arabidopsis. Evidence that transcripts of the AGL15 gene are present in developing embryos is provided by reverse transcription-PCR using isolated Arabidopsis embryos (Heck and Fernandez, unpublished results) and by in situ hybridization (Rounsley et al., *Plant Cell* 7:1259–1269, 1995).

The AGL15 gene is one of 24 members of the MADS domain genes that have been isolated from Arabidopsis. The AGL15 gene is the only Arabidopsis MADS domain regulatory factor identified to date that is preferentially expressed in developing embryos (Rounsley et al., *Plant Cell* 7:1259–1269, 1995). A comparison of the predicted amino acid sequence of AGL15 to predicted amino acid sequences encoded by other Arabidopsis MADS domain genes showed a high percentage of amino acid identity in the 56-amino acid MADS domain, a lower percentage of amino acid identity in the K domain, and a divergence of amino acid sequences in the C-terminal region.

Generation of AGL-15-Specific Antibodies

AGL15-specific antigen was obtained as follows. Nucleotide sequences downstream of the MADS domain of the *B. napus* AGL15-1 gene were amplified from the *B. napus* transition stage embryo cDNA library. The primers used in the amplification reaction were AGL15-1-specific oligonucleotides that were flanked by NcoI and BamHI restriction sites, and which incorporated a termination codon. The PCR product, which corresponded to amino acid residues 62 to 258 of SEQ ID NO:3, was ligated to a linearized expression vector pET-15b (Novagen, Madison, Wis.) with compatible ends.

Overexpression of truncated *B. napus* AGL15-1 was accomplished by transformation of the expression host BL21(DE3) and induction with 1 mM isopropyl β-D-thiogalactopyranoside (X-Gal) (Perry and Keegstra, *Plant Cell* 6:93–105, 1994). The polypeptide was recovered from isolated inclusion bodies by solubilization for five minutes at room temperature in a solution containing 8 M urea and 10 mM β-mercaptoethanol in a 50 mM Tris-HCl, 5 mM $MgCl_2$ buffer, pH 7.6. The solubilized protein was further purified by electrophoresis on two successive preparative Pro-Sieve agarose gels (FMC, Rockland, Me.). A protein band corresponding to truncated AGL15-1 was excised from the gel and used to immunize rabbits at the University of Wisconsin-Madison Medical School Animal Care Unit.

Blot-affinity purification (Tang, *Methods in Cell Biology*, 37:95–104, 1993) was used to purify antibodies that recognized truncated AGL15-1 for use in protein gel blot analyses, described below. Antibodies to be used in immunohistochemistry studies were prepared as follows. Immune and preimmune sera were preadsorbed to remove serum components that bind nonspecifically to fixed plant tissues (Jack et al., *Cell* 76:703–716, 1994). Pieces (approximately 4 $mm^2$) of fully expanded Brassica leaves in which AGL15 is not expressed were fixed for one hour under vacuum with 4% (w/v) freshly prepared paraformaldehyde and 0.02% (v/v) Triton X-100 in 50 mM potassium phosphate buffer, pH 7. The leaf pieces were washed for several hours in a large volume, with multiple changes, of PBST buffer (237 mM NaCl, 2.7 mM KCl, 4.3 mM $Na_2HPO_4$, 1.4 mM $KH_2PO_4$, 0.1% Tween 20, pH 7.3). A solution consisting of 10% (v/v) preimmune or immune serum, 0.05% (w/v) BSA fraction V in 0.9×PBST was added to the fixed leaf pieces (approximately 5 ml of solution per gram of leaf tissue) and incubated overnight at 4° C. with gentle agitation. The preadsorbed serum was removed by aspiration, and sodium azide was added to make the serum 0.05% (w/v) sodium azide. The serum was stored at 4° C. Serum prepared in this manner could be used for several months.

Protein extracts of developing plant embryos for immunoblot analysis were prepared as described in Heck, et al. (Heck, et al., *Plant Cell* 7:1271–1282, 1995). Plant tissue sections were prepared and immunohistochemistry performed as described in Perry, et al. (Perry, et al., *Plant Cell* 8:1977–1989, 1996).

Several lines of evidence indicate that the AGL15 antiserum is specific for AGL15. Gel blot analysis demonstrated that the AGL15 antiserum does not recognize AGL2, which is the only other MADS domain protein reported to be expressed during embryogenesis in Arabidopsis (Flanagan and Ma, *Plant Mol. Biol.* 26:581–595, 1994). Immunohistochemical studies employing Brassica embryos demonstrated that AGL15 antiserum exhibits nuclear staining in developing embryos. However, antiserum depleted of AGL15-specific antibodies by preadsorption with overexpressed AGL15 did not exhibit nuclear staining (Perry and Fernandez, unpublished results). To determine whether the antibodies recognize and bind other MADS domain proteins, sections of young floral buds were incubated with antiserum. The antibodies did not label nuclei in developing floral organs, a developmental context in which many different MADS domain family members are expressed in Arabidopsis.

Conservation of AGL15 Structural Elements within Angiosperms

If the AGL15 gene product plays an important role in embryo development, it is reasonable to expect that a related protein performs similar functions in embryos of many different groups of flowering plants. This hypothesis was tested using the AGL15-specific antibodies in combination with immunoblots of soluble protein extracts from numerous groups of flowering plants, and immunohistochemistry, using sections of plant embryos and young seeds. In immunoblot analysis, the AGL15 antibodies were found to bind to one, or at most two, protein band(s) from all tested plant embryos. Immunohistochemistry using sections from developing embryos from a variety of plant showed that the AGL15-specific antibody bound to embryo sections from all tested plant groups, and that the staining was localized to the nuclei. These results are summarized in Table 1.

TABLE 1

Detection and Localization of AGL15 Proteins in Flowering Plants

| Plant | Tissue |
| --- | --- |
| Brassica napus (oilseed rape) | embryo/endosperm (seed) inflorescence, abscission zone, developing pollen, somatic embryo young seedling |
| Arabidopsis thaliana | embryo/endosperm (seed) inflorescence, young seedling |
| Broccoli | inflorescence |
| Cauliflower | inflorescence |
| Cleome | inflorescence |
| Polanisia | inflorescence |
| Papaya | embryos |
| Pepper | seed |
| Zea mays (maize) | embryo/endosperm (seed) |
| Potato | abscission zone |

TABLE 1-continued

Detection and Localization of AGL15 Proteins in Flowering Plants

| Plant | Tissue |
| --- | --- |
| Tomato | abscission zone |
| Wheat | wheat germ (embryos) |
| Dandelion | embryos (seed) |
| Alfalfa | leaves and somatic embryos |
| Rice | embryos |
| Chicory | leaves and somatic embryos vegetative shoot in culture |

The temporal and spatial patterns of expression of AGL15 are consistent with it being a factor in embryo specification. AGL15 mRNA is present throughout embryo development and maturation, and is present in all cells of the embryo. This pattern of expression suggests that AGL15 may have a global regulatory function, such as the promotion of embryo-specific programs or the inhibition of postgermination programs (Heck et al. *Plant Cell* 7:1271–1282, 1995). The ubiquitousness and the high degree of conservation of the AGL15 gene among plants suggest that it has an essential function in plant development. To facilitate research into the role of AGL15 in plant development, transgenic plants in which AGL15 was overexpressed were created.

Generation of Genetic Constructs and Transformation of Plants

Two constructs containing an AGL15 gene operably linked to a promoter functional in plants were created using the transformation vector pBI121 (Clontech). An AGL15 protein-encoding DNA sequence (SEQ ID NO:1) was placed under the control of the cauliflower mosaic virus (CaMV) 35S promoter. This was accomplished by replacing the GUS gene of pBI121 with the Arabidopsis AGL15 cDNA sequence (SEQ ID NO:1), which contains an 807-bp ORF, as well as 18 bp of the 5' untranslated region (UTR) and 245 bp of the 3' UTR. The construct was designated p35S-AGL15 (DF164) (FIG. 1A). A second construct, designated p35S-AGL15+ (DF121), was made by replacing a BsmI-NsiI fragment within the ORF of the Arabidopsis AGL15 cDNA insert in the DF164 construct with the first three introns of the genomic AGL15 gene (FIG. 1B). This construct was made with the expectation that it would afford higher levels of AGL15 expression, because introns are sometimes necessary to achieve high levels of gene expression.

Constructs were transformed into Arabidopsis with Agrobacterium strain GV3101 using the vacuum infiltration protocol (Bechtold, et al., *Comptes Rendus de l'Academie des Sciences Serie III Sciences de la Vie* 316:1194–1199, 1993) and modifications introduced by A. Bent to simplify plant handling. Transformants (T1 generation) were selected on GM plates supplemented with 75 µg/ml kanamycin prior to transfer to soil. The number of transgenic loci within each line was determined by segregation of kanamycin resistance (using 50 µg/ml kanamycin) in T2 progeny.

The relative levels of ectopic expression were determined by preparing soluble protein extracts from leaves, which normally do not accumulate AGL15, and subjecting the protein extracts to immunoblot analysis. Transformation of plants with the DF164 construct yielded transgenic plants in which AGL15 was constitutively expressed at low to intermediate levels. Transformation of plants with the DF121 construct, which contains three introns, yielded transformants in which AGL15 was constituitively expressed at intermediate to high levels.

Characterization of Transgenic Plants

In initial experiments, transformation of Arabidopsis plants with DF164 yielded 48 lines carrying the construct. Of these 48 lines, only one line showed an obvious phenotypic distinction in the T1 generation. The same phenotypic alteration was seen in the T2 generation in several more lines, presumably because the DF164 copy number increased after the T1 plants selfed. The phenotypically distinct plants were found to have an intermediate level of overexpression of the AGL15 gene. Several other lines of DF164 transformants that exhibit the phenotype and intermediate levels of AGL15 expression have been obtained in subsequent trials; characterization of these lines is currently underway. Transformation of Arabidopsis with DF121 yielded 38 lines, of which 17 demonstrated obvious phenotypes that corresponded to intermediate or high levels of overexpression in the T1 generation.

A total of 20 lines exhibited altered phenotypes associated with AGL15 overexpression. These phenotypes fell into two classes, which corresponded to different levels of overexpression, as assessed by immunoblot analysis of leaf soluble protein samples. Class 1 plants, in which AGL15 was overexpressed at intermediate levels, showed a variety of effects. The effects observed include: 1) delayed silique (fruit) maturation; 2) increased numbers of flowers and fruits; 3) delayed floral organ senescence/abscission; and 4) delayed senescence of cut flowers and inflorescences.

Class 2 plants, in which AGL15 was overexpressed at high levels, showed a variety of severe (abnormal) phenotypes, as well as many of the features characteristic of the Class 1 plants. Both the leaves and cotyledons of Class 2 plants appeared to have expansion problems, and produced "cupped" organs with upturned margins. The flowers were semi- or completely sterile and showed features that suggest that high levels of AGL15 interfere with the function of other MADS domain regulatory factors. Floral petals were green. In the two lines that demonstrated the highest level of overexpression, up to 30% of the flowers had 4–5, rather than 2, carpels and they contained another inflorescence within the fused carpels. The two fused carpels are also carried on an elongated internode. Seeds produced by outcrossing strong overexpressors were abnormally shaped but contained normal levels of storage protein. However, they appeared to be dessication intolerant and did not germinate when they were left on the plant until the siliques were fully dry.

Effects of Overexpression of AGL15 on Fruit Maturation

Fruit maturation in transgenic Arabidopsis plants that contained a single copy of DF164 and that exhibited intermediate overexpression of AGL15 was compared with fruit maturation in untransformed Arabidopsis controls. Transgenic Arabidopsis plants that exhibited high levels of AGL15 overexpression were self-sterile and did not produce fruit. In assessing the effects of AGL15 on fruit maturation, the "time to maturity" was defined as the number of days from pollination to full maturity. Fruits were considered to have reached "full maturity" when they were completely brown. The time to maturity was approximately 50% longer in transgenic plants than in untransformed controls (Table 2).

TABLE 2

Effects of AGL15 Overexpression on Fruit Maturation in Arabidopsis

| Genotype | Time (days) from pollination to full maturity | |
|---|---|---|
| | Experiment 1 | Experiment 2 |
| wildtype | 17.25 ± 0.9 (N = 59) | 18.4 ± 0.6 (N = 29) |
| transgenic | 24.6 ± 0.7 (N = 17) | 26.2 ± 0.8 (N = 44) |

Effect of AGL15 Overexpression on Fruit Production

Transgenic Arabidopsis plants containing a single copy of the DF164 construct were grown adjacent to untransformed Arabidopsis control plants until the plants had matured and dried fully. The number of siliques (fruit) produced by each plant was determined. Only those siliques that showed good seed fill and that were produced in the initial phase of inflorescence growth (before the point of global arrest, when the meristems "pause") were counted as "fruit". A comparison of the number of siliques produced showed that the transgenic plants produced approximately 50% more fruit than the untransformed controls (Table 3).

TABLE 3

Effects of AGL15 Overexpression on Fruit Production

| Genotype | No. of siliques per plant |
|---|---|
| wildtype | 381 ± 64 (N = 5) |
| transgenic | 750 ± 149 (N = 5) |

Effect of AGL15 Overexpression on Floral Organ Abscission and Senescence

In untransformed Arabidopsis plants, petals and sepals undergo abscission from two to three days after pollination. In transgenic plants in which AGL15 is overexpressed at intermediate levels, petals and sepals remain attached for from 1.5 to 2 weeks following pollination. The floral organs remain turgid and show no sign of senescence during this period. Transgenic plants in which AGL15 was expressed at high levels showed delayed abscission and senescence that was more dramatic than plants with intermediate levels of expression. However, the flowers of these plants were not normal, in that the floral petals were green.

Effects of Overexpression of AGL15 on Cut Flower Longevity

The effects of AGL15 overexpression on the longevity of cut flowers was assessed as follows. Flowers and/or inflorescences were removed from transgenic and untransformed plants and placed on filter paper moistened with distilled water, and the filter paper transfered to a dish that was then sealed to maintain high humidity. The sealed dishes containing the cut flowers were incubated under ambient temperature and light conditions. Flowers from untransformed plants turned brown within a few days. Flowers from transgenic plants lived up to 2.5 weeks without showing signs of senescence, in that the sepals and stems remained green and the petals remained turgid. As long as high humidity was maintained, the cut flowers exhibited no sign of wilting. However, growth of contaminating mold necessitated termination of the experiments at around three weeks, prior to any sign of floral wilting. The experiment was repeated several times, with 10 to 20 flowers in each experimental set. The effect was even more pronounced in plants overexpressing AGL15 at high levels, in that after 2.5 to 3 weeks, even the oldest flowers at the base of the cut inflorescence had the appearance of newly opened flowers. It is speculated that the more pronounced effect observed in plants in which AGL15 is expressed at high levels is related to the reduced fertility that these plants exhibit.

Because research in the area of flower senescence and abscission has focused on the manipulation of ethylene levels, the response of the transgenic plants to ethylene was assessed using the cut flower assay. When transgenic plants in which AGL15 is overexpressed and which exhibited delayed floral abscission were exposed to ethylene, their petals fell off the plant. Arabidopsis mutant etr-1 plants, which do not lose their flower petals upon exposure to ethylene, were included in the cut flower assay. These plants retain petals and sepals for a few days longer than wild type Arabidopsis plants, but not as long as the transgenic plants overexpressing AGL15. These results suggest that AGL15 may affect some aspect of the senescence/abscission process that is ethylene-independent.

We claim:

1. A transgenic flowering plant comprising in its genome a genetic construct comprising an Arabidoysis or Brassica AGL15 sequence and a promoter that promotes expression of the AGL15 sequence in the plant, the promoter not being natively associated with the AGL15 sequence.

2. The plant of claim 1, wherein the construct comprises the AGL15 sequence of SEQ ID NO:1.

3. The plant of claim 1, wherein the construct comprises in 5' to 3' order a CaMV 35S promoter, the AGL15 sequence of SEQ ID NO:1, a nopaline synthase terminator, and a kanamycin resistance marker.

4. A transgenic seed of a flowering plant, wherein the seed comprises in its genome a genetic construct comprising an Arabidopsis or Brassica AGL15 sequence and a promoter that promotes expression of the AGL15 sequence in flowering plants, the promoter not being natively associated with the AGL15 sequence.

5. The seed of claim 4, wherein the construct comprises the AGL15 sequence of SEQ ID NO:1.

6. The seed of claim 4, wherein the construct comprises in 5' to 3' order a CaMV 35S promoter, the AGL15 sequence of SEQ ID NO:1, a nopaline synthase terminator, and a kananmycin resistance marker.

7. A transgenic plant cell of a flowering plant, wherein the plant cell comprises in its genome a genetic construct comprising an Arabidopsis or Brassica AGL15 sequence and a promoter that promotes expression of the AGL15 sequence in flowering plants, the promoter not being natively associated with the AGL15 sequence.

8. The plant cell of claim 7, wherein the construct comprises the AGL15 sequence of SEQ ID NO:1.

9. The plant cell of claim 7, wherein the construct comprises in 5' to 3' order a CaMV 35S promoter, the AGL15 sequence of SEQ ID NO:1, a nopaline synthase terminator, and a kanamycin resistance marker.

10. A genetic construct comprising an Arabidopsis or Brassica AGL15 sequence and a promoter that promotes expression of the sequence in flowering plants, the promoter not being natively associated with the AGL15 sequence.

11. The genetic construct of claim 10, wherein the AGL 15 sequence is SEQ ID NO:1.

12. The genetic construct of claim 10, wherein the promoter comprises the CaMV 35S promoter and the AGL15 sequence comprises SEQ ID NO:1.

13. The genetic construct of claim 12 additionally comprising a nopaline synthase terminator and a kanamycin resistance marker.

14. A transgenic flowering plant comprising in its genome a genetic construct comprising an Arabidopsis or Brassica AGL15 sequence and a promoter that promotes expression of the AGL15 sequence in the plant, the promoter not being natively associated with the AGL15 sequence, wherein the AGL15 sequence is selected so that the plant exhibits at least one phenotype selected from the group of increased number of flowers and fruits, delayed maturation of fruit, delayed floral organ senescence, delayed floral organ abscission, delayed senescence of cut flowers, and delayed senescence of inflorescences, relative to the same plant without the AGL15 sequence and the promoter not natively associated with the AGL15 sequence.

15. The transgenic flowering plant of claim 14 wherein the AGL15 sequence encodes a protein that binds to a polyclonal antibody produced using amino acids 62–258 of SEQ ID NO:3 as antigen.

16. A transgenic seed of a flowering plant comprising in its genome a genetic construct comprising an Arabidopsis or Brassica AGL15 sequence and a promoter that promotes expression of the AGL15 sequence in the plant, the promoter not being natively associated with the AGL15 sequence, wherein the AGL15 sequence is selected so that the plant resulting from the seed exhibits at least one phenotype selected from the group of increased number of flowers and fruits, delayed maturation of fruit, delayed floral organ senescence, delayed floral organ abscission, delayed senescence of cut flowers, and delayed senescence of inflorescences, relative to the same plant without the AGL15 sequence and the promoter not natively associated with the AGL15 sequence.

17. The transgenic seed of a flowering plant of claim 16 wherein the AGL15 sequence encodes a protein that binds to a polyclonal antibody produced using amino acids 62–258 of SEQ ID NO:3 as antigen.

18. A transgenic plant cell of a flowering plant comprising in its genome a genetic construct comprising an Arabidopsis or Brassica AGL15 sequence and a promoter that promotes expression of the AGL15 sequence in the plant, the promoter not being natively associated with the AGL15 sequence, wherein the AGL15 sequence is selected so that the plant resulting from the plant cell exhibits at least one phenotype selected from the group of increased number of flowers and fruits, delayed maturation of fruit, delayed floral organ senescence, delayed floral organ abscission, delayed senescence of cut flowers, and delayed senescence of inflorescences, relative to the same plant without the AGL15 sequence and the promoter not natively associated with the AGL15 sequence.

19. The transgenic plant cell of a flowering plant of claim 18 wherein the AGL15 sequence encodes a protein that binds to a polyclonal antibody produced using amino acids 62–258 of SEQ ID NO:3 as antigen.

20. A genetic construct comprising an Arabidopsis or Brassica AGL15 sequence and a promoter that promotes expression of the AGL15 sequence in a flowering plant, the promoter not being natively associated with the AGL15 sequence, wherein the AGL15 sequence is selected so that the plant exhibits at least one phenotype selected from the group of increased number of flowers and fruits, delayed maturation of fruit, delayed floral organ senescence, delayed floral organ abscission, delayed senescence of cut flowers, and delayed senescence of inflorescences, relative to the same plant without the AGL15 sequence and the promoter not natively associated with the AGL15 sequence.

21. The genetic construct of claim 20 wherein the AGL15 sequence encodes a protein that binds to a polyclonal antibody produced using amino acids 62–258 of SEQ ID NO:3 as antigen.

22. The transgenic flowering plant of claim 1 wherein the AGL15 sequence encodes a protein that binds to a polyclonal antibody produced using amino acids 62–258 of SEQ ID NO:3 as antigen.

23. (New) The transgenic seed of claim 4 wherein the AGL15 sequence encodes a protein that binds to a polyclonal antibody produced using amino acids 62–258 of SEQ ID NO:3 as antigen.

24. The transgenic plant cell of claim 7 wherein the AGL15 sequence encodes a protein that binds to a polyclonal antibody produced using amino acids 62–258 of SEQ ID NO:3 as antigen.

25. The genetic construct of claim 10 wherein the AGL15 sequence encodes a protein that binds to a polyclonal antibody produced using amino acids 62–258 of SEQ ID NO:3 as antigen.

26. A method of causing a flowering plant to exhibit at least one phenotype selected from the group of increased numbers of flowers and fruits, delayed maturation of fruit, delayed floral organ senescence, delayed floral organ abscission, delayed senescence of cut flowers, and delayed senescence of cut inflorescences, comprising:

(a) transforming a cell of a plant with a genetic construct comprising an Arabidopsis or Brassica AGL15 sequence and a promoter that promotes expression of the AGL15 sequence in the plant, the promoter not being natively associated with the AGL15 sequence;

(b) regenerating the transformed plant cell to provide a plant; and (c) identifying a transformed plant which expresses the coding sequence so as to exhibit at least one phenotype selected from the group of increased numbers of flowers and fruits, delayed maturation of fruit, delayed floral organ senescence, delayed floral organ abscission, delayed senescence of cut flowers, and delayed senescence of cut inflorescences, relative to the same plant without the AGL15 sequence and the promoter not natively associated with the AGL15 sequence.

27. The method of claim 26, wherein the AGL15 sequence encodes a protein that binds to a polyclonal antibody produced using amino acids 62–258 of SEQ ID NO:3 as antigen.

28. A method of causing a flowering plant to express at increased levels a protein that binds to a polyclonal antibody produced using amino acids 62–258 of SEQ ID NO:3 as antigen, comprising:

(a) transforming a cell of a plant with a genetic construct comprising an Arabidopsis or Brassica AGL15 sequence, wherein the AGL15 sequence encodes a protein that binds to a polyclonal antibody produced using amino acids 62–258 of SEQ ID NO:3 as antigen, and a promoter that promotes expression of the AGL15 sequence in the plant, the promoter not being natively associated with the AGL15 sequence;

(b) regenerating the transformed plant cell to provide a plant; and (c) identifying a transformed plant which expresses the AGL15 sequence so as to express at increased levels a protein that binds to the polyclonal antibody, relative to the same plant without the AGL15 sequence and the promoter not natively associated with the AGL15 sequence.

* * * * *

UNITED STATES PATENT AND TRADEMARK OFFICE
CERTIFICATE OF CORRECTION

PATENT NO.     : 6,133,435
DATED          : October 17, 2000
INVENTOR(S)    : Fernandez et al.

It is certified that error appears in the above-identified patent and that said Letters Patent is hereby corrected as shown below:

Title page,
Replace "[76]" with -- [75] -- within Inventor field;
Delete "1034 McKenna Blvd., Unit #5" and "53719" within Inventor field;
Delete "2200 Divot Dr." and "63131-3201" within Inventor field;
Insert -- [73] Assignee: Wisconsin Alumni Research Foundation, Madison, Wis. --;

Item [56], References Cited, OTHER PUBLICATIONS, replace "Medicated" with -- Mediated -- within Bechtold publication cite;
After "vol." insert -- 107 -- within Matzke and Matzke publication cite;
After "Matzke and Matzke" insert the title -- How and Why Do Plants Inactivate Homologous (Trans)genes ? --;
Delete "Heck etal. The Plant Cell. 7:127111-1282, 1995." as a duplicative publication cite;
Delete "Perry et al. The Plant Cell. 1996. 8: 1977-1989" as a duplicative publication cite;
Insert title -- SILENCING OF WAXY GENES IN RICE CONTAINING WX TRANSGENES -- after "Itoh et al."; insert -- TRANSGENE INACTIVATION: PLANTS FIGHT BACK! -- after "Finnegan and McElroy."; insert -- AGROBACTERIUM TUMEFACIENS-MEDIATED TRANSFORMATION OF ARABIDOPSIS THALIANA ROOT EXPLANTS BY USING KANAMYCIN SELECTION -- after "Valvekens et al."

Signed and Sealed this

Ninth Day of July, 2002

*Attest:*

*Attesting Officer*

JAMES E. ROGAN
*Director of the United States Patent and Trademark Office*